(12) United States Patent
Dockrill et al.

(10) Patent No.: US 9,927,332 B2
(45) Date of Patent: Mar. 27, 2018

(54) SLIDE TRANSPORT SYSTEM

(71) Applicant: LEICA BIOSYSTEMS MELBOURNE PTY LTD, Mount Waverly, Victoria (AU)

(72) Inventors: Mark Brian Dockrill, Chadstone (AU); Martin Limon, Richmond (AU); Mark Wilcock, Parkdale (AU); Steve Collins, Wheelers Hill (AU); Brendyn Rodgers, Blackburn (AU)

(73) Assignee: LEICA BIOSYSTEMS MELBOURNE PTY LTD, Mount Waverly, Victoria (AU)

( * ) Notice: Subject to any disclaimer, the term of this patent is extended or adjusted under 35 U.S.C. 154(b) by 0 days.

(21) Appl. No.: 14/439,788

(22) PCT Filed: Nov. 1, 2013

(86) PCT No.: PCT/AU2013/001263
§ 371 (c)(1),
(2) Date: Apr. 30, 2015

(87) PCT Pub. No.: WO2014/066946
PCT Pub. Date: May 8, 2014

(65) Prior Publication Data
US 2015/0300931 A1    Oct. 22, 2015

Related U.S. Application Data

(60) Provisional application No. 61/721,257, filed on Nov. 1, 2012.

(51) Int. Cl.
*G01N 35/10* (2006.01)
*G01N 1/31* (2006.01)
*G01N 35/00* (2006.01)

(52) U.S. Cl.
CPC ......... *G01N 1/312* (2013.01); *G01N 35/0099* (2013.01); *G01N 35/00732* (2013.01);
(Continued)

(58) Field of Classification Search
CPC ............... G01N 1/312; G01N 35/0099; G01N 2035/00039
See application file for complete search history.

(56) References Cited

U.S. PATENT DOCUMENTS 5,039,615 A * 8/1991 Takahata .......... G01N 35/00029
422/63
6,739,448 B1 * 5/2004 Bevirt .................... G01N 35/04
198/468.8

(Continued)

FOREIGN PATENT DOCUMENTS

EP      0287005 A2    10/1988
WO   2012/064873 A1    5/2012

OTHER PUBLICATIONS

International Search Report for PCT/AU2013/001263 dated Jan. 13, 2014.

(Continued)

*Primary Examiner* — P. Kathryn Wright
(74) *Attorney, Agent, or Firm* — Sughrue Mion, PLLC

(57) ABSTRACT

A slide transport system for an automated slide treatment apparatus having slide treatment modules for receiving slides and a fluid dispensing robot configured by a controller to dispense reagents to the slides is disclosed. The slide transport system includes a slide transport robot configured by the controller to move the slides to and from the slide treatment modules and a slide transport device disposed on the slide transport robot and configured by the controller to releasably hold the slides. A slide handling head on the slide transport robot moves a closure body of a slide treatment module from a normally closed to an open position to move (Continued)

slides in the slide treatment module. The slide transport device is configured by the controller to release a slide when located in the slide treatment module, when the closure body is in the open position.

15 Claims, 12 Drawing Sheets

(52) U.S. Cl.
CPC ............... *G01N 35/1002* (2013.01); *G01N 2035/00039* (2013.01); *G01N 2035/00851* (2013.01); *G01N 2035/1051* (2013.01)

(56) References Cited

U.S. PATENT DOCUMENTS

| 2007/0172396 | A1* | 7/2007 | Neeper ............ G01N 35/00732 422/400 |
| 2010/0178668 | A1* | 7/2010 | Elliot ..................... B01L 3/545 435/40.52 |
| 2011/0136135 | A1 | 6/2011 | Larsen et al. |
| 2012/0149050 | A1 | 6/2012 | Lapen et al. |

OTHER PUBLICATIONS

Communication dated Jun. 3, 2016, from the European Patent Office in counterpart European application No. 13851009.4.

* cited by examiner

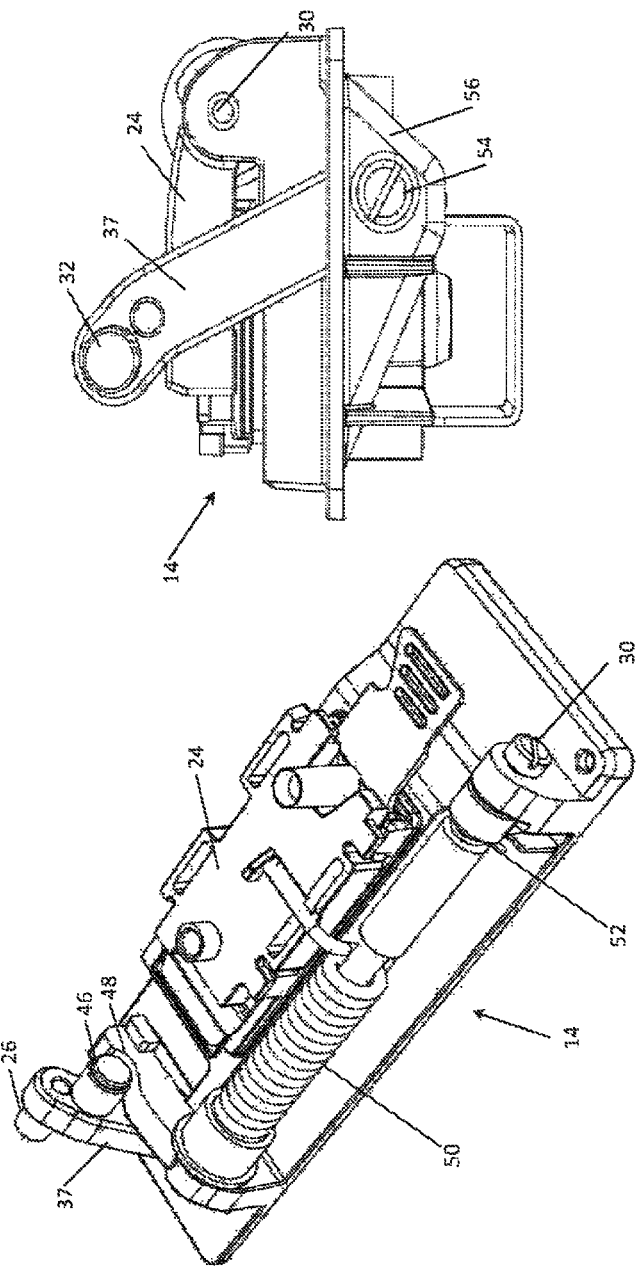

SLIDE TRANSPORT SYSTEM

CROSS REFERENCE TO RELATED APPLICATIONS

This application is a National Stage of International Application No. PCT/AU2013/001263 filed Nov. 1, 2013, claiming priority based on U.S. Provisional Patent Application No. 61/721,257, filed Nov. 1, 2012, the contents of all of which are incorporated herein by reference in their entirety.

TECHNICAL FIELD

The present invention relates to a slide transport system for an automated slide treatment apparatus for treating one or more tissue samples disposed on slides. The slide treatment apparatus includes a plurality of slide treatment modules arranged to receive ones of the slides and at least one fluid dispensing robot configured by a controller to dispense a plurality of reagents to the slides received in the slide treatment modules to treat the one or more tissue samples.

The present invention relates particularly, but not exclusively, to a slide transport robot of the slide transport system moving a closure body of one of the slide treatment modules from a normally biased closed position to an open position when the robot moves one of the slides to the slide treatment module to locate the slide in the slide treatment module. The one or more tissue samples on the slide can thus be treated by dispensing designated reagents to the slide when the slide is located in the slide treatment module and the slide treatment module is in the closed position.

BACKGROUND TO THE INVENTION

Existing tissue sample treatment methods, in some applications, comprise a number of steps that are performed manually. For example, in immunologic applications, such as in-situ hybridization (ISH) and immunohistochemical (IHC) applications, some steps, including baking a sample onto a slide, dewaxing, and epitope retrieval are performed manually by an operator to treat the tissue sample before it can be used in a staining apparatus for staining the tissue sample according to a predetermined staining protocol.

Immunohistochemical staining and in situ nucleic acid analysis are tools used in histological diagnosis and the study of tissue morphology. Immunohistochemical staining relies on the specific binding affinity of antibodies with epitopes in tissue samples, and the increasing availability of antibodies which bind specifically with unique epitopes present only in certain types of diseased cellular tissue. Immunohistochemical staining involves a series of treatment steps conducted on a tissue sample (typically a section) mounted on a glass slide to highlight, by selective staining, certain morphological indicators of disease states.

Typical treatment steps include pre-treatment of the tissue sample to reduce non-specific binding, antibody treatment and incubation, enzyme labelled secondary antibody treatment and incubation, substrate reaction with the enzyme to produce a fluorophore or chromophore highlighting areas of the tissue sample having epitopes binding with the antibody, counterstaining, and the like. Between each treatment step, the tissue sample must be rinsed to remove unreacted residual reagent from the prior step. Most treatment steps involve a period of incubation typically conducted at ambient temperature of around 25° C. up to around 40° C., while cell conditioning steps are typically conducted at somewhat higher temperatures, e.g. 90° C. to 100° C. In-situ DNA analysis relies upon the specific binding affinity of probes (DNA binding proteins) with unique nucleotide sequences in cell or tissue samples and similarly involves a series of process steps, with a variety of reagents and process temperature requirements. Some specific reactions involve temperatures up to 120° C. to 130° C.

Attempts have been made to automatically treat tissue samples disposed on slides for immunologic applications using, for example, an automated tissue sample staining apparatus. In an existing example, the automated staining apparatus treats tissue samples using reagents to treat the sample before staining the samples on the slides. The treatment of the samples is performed automatically by one or more robots configured to dispense reagents to slides in a predetermined sequence according to a staining protocol. These existing automated staining apparatuses, however, tend to be bulky to accommodate the different treatment modules for the different treatment steps and thus take up a large amount of laboratory real estate. Furthermore, due to the ever increasing numbers of histological test requests and biopsy samples, there are now significant pressures on laboratories to decrease turnaround time of treating tissue samples.

SUMMARY

According to one aspect of the present invention, there is provided a slide transport system for an automated slide treatment apparatus for treating one or more tissue samples disposed on slides including a plurality of slide treatment modules arranged to receive ones of the slides and at least one fluid dispensing robot configured by a controller to dispense a plurality of reagents to said ones of the slides received in the slide treatment modules to treat said one or more tissue samples respectively, the slide transport system including: a slide transport robot configured by the controller to move the slides to and from the slide treatment modules; and a slide transport device disposed on the slide transport robot and configured by the controller to releasably hold the slides, wherein the slide transport robot includes a slide handling head arranged to move a closure body of one of the slide treatment modules so as to move the closure body normally held in a closed position to an open position when the slide transport robot is configured by the controller to move one of the slides to the slide treatment module; and wherein the slide transport device is configured by the controller to release the slide so as to locate the slide in the slide treatment module when the closure body is in the open position.

In an embodiment, the closure body is normally biased in the closed position to hold the closure body in the closed position. In another embodiment, the closure body is detained in the closed position with a detent protruding from a detention arm that is arranged to cooperate with a recess in the closure body in the closed position. In this embodiment, for example, the closure body is normally biased in the open position and the detent resists the bias to open. Alternatively, or in addition, the detent prevents the closure body of the slide treatment module from being accidentally opened.

In an embodiment, the slide handling head is further arranged to contact against a bearing surface of the closure body to move the closure body to the open position. Also, the slide handling head may have a corresponding surface for contacting the bearing surface of the closure body. The slide handling head and the closure body are thus preferably shaped so as to efficiently and economically open and close the closure body of the slide treatment modules for slides to be located therein.

In another embodiment, the slide transport robot is configured to move in the x, y and z axes. In this embodiment, the slide transport robot is a gantry robot with rails in each of the corresponding axes enabling the robot to move in those directions. That is, the gantry robot is configured to move along the rails in the x and y directions and to move in the z direction (e.g. up and down) so as to locate the slide in a designated slide treatment module and to remove the slide from the designated slide treatment module. In another embodiment, the slide transport robot is an articulated robot arm that can move in the x, y and z axes but is not limited to Cartesian movement only, as will be appreciated by persons skilled in the art.

In an embodiment, the slide handling head contacts against the bearing surface of the closure body of one of the slide treatment modules to move the closure body to the open position when the slide transport robot moves in one direction, here the x axis. In this embodiment, the slide treatment modules are aligned lengthwise in the slide treatment apparatus along the x axis so that the slide handling head of the slide transport robot can move the closure body to the open position when the slide transport robot moves in the x axis. It will be appreciated by those persons skilled in the art that, in another example, the slide treatment modules are arranged width-wise along the y axis of the apparatus and, in this case, the slide handling head of the slide transport robot contacts against the bearing surface of the closure body and moves the closure body to the open position when the slide transport robot moves in the y axis. In any case, the slide transport robot moves in the z axis to locate the slide in the slide treatment module when the closure body is held in the open position by the slide handling head. That is, the robot lowers the slide to a mounting surface of the slide treatment module arranged to receive the slide in a predetermined position and the closure body is then returned to the closed position by moving the robot so the tissue samples on the slide can be treated (e.g. stained) by dispensing the designated reagents.

In an embodiment, the slide transport robot further moves in the x and y axes when the closure body is in the open position to further locate the slide in the slide treatment module—in the predetermined position—using at least one reference datum point disposed on the slide treatment module. In addition, the slide transport robot is further configured to stop moving the slide in the slide treatment module in the x and/or y axes when the slide touches the at least one reference datum point. It will be appreciated by those persons skilled in the art that the reference datum points are protrusions in the slide treatment module and the slide transport robot is further configured to stop moving the slide in the slide treatment module in the z axis when the slide touches the mounting surface. In another example, the slide transport robot is further configured to stop moving the slide in the slide treatment module in the x and/or y axes when it senses the at least one reference datum point. In yet another example, spring means such as spring scissor or finger means are disposed at the reference datum points to ensure the slide is placed in the slide treatment module in its correct position. In yet another example, spring means such as spring scissor or finger means are disposed in opposition to the reference datum points to ensure the slide is placed in the slide treatment module in its correct position.

It will also be appreciated that the slide is typically rectangular in shape, having a width and a length substantially greater than the width, and the slide treatment modules have a corresponding shape. In one example, the reference datum points include one reference datum point along the width of the slide treatment module to stop the slide moving in the y direction and two reference datum points along the length of the slide treatment module so that the slide transport robot is configured to stop moving in the x direction when it hits one or both of these reference datum points. It will further be appreciated that the slide transport robot is further configured to make rotation adjustments for the slide so that it is located in the predetermined position on the mounting surface of the slide treatment module.

In addition, the slide handling head maintains contact against the bearing surface of the closure body of one of the slide treatment modules whilst the bias of the closure body moves the closure body to the closed position when the slide transport robot moves in the x axis after the slide transport robot locates a slide in the slide treatment module. Also, the slide handling head maintains contact against the bearing surface of the closure body when the slide transport robot moves in the x axis after the slide transport robot removes a slide from the slide treatment module. That is, the closure body of the slide treatment module is biased to the closed position and reverts to the closed position after the slide transport robot locates the slide in the slide treatment module for treatment of the tissue sample on the slide or after the slide transport robot removes the slide from the slide treatment module.

It will be appreciated by those persons skilled in the art that the slide treatment module includes a biasing means, such as a spring, for applying the biasing force to the closure body. The biasing means can also bias the closure body to the closed position to achieve a seal with the slide and the mounting surface to create, for example, a sealed reaction chamber for treating the tissue samples on the slide.

Furthermore, in one embodiment, the slide treatment module includes a cover member—of the type described in the co-pending U.S. provisional patent application 61/721,280 entitled "Slide Staining Assembly and Cover Member" having a filing date of 1 Nov. 2012, the contents of which are hereby incorporated herein by reference—for forming the reaction chamber with the slide.

In an embodiment, the slide handling head contacts against the bearing surface of the closure body of one of the slide treatment modules to pivot the closure body to the open position about a pivot disposed on the slide treatment module. That is, the slide handling head of the slide transport robot, moving in the x axis, moves towards the pivot of the slide treatment module to pivot the closure body to the open position against the action of the biasing means. It will be appreciated by those persons skilled in the art, however, that the opening of closure body by the slide handling head need not only involve pivoting, the separation of the closure body from its mounting surface could be achieved by, say, lifting the closure body or lowering the mounted surface, as well as sliding the two parts relate to each other to accommodate placement of the slide by action of the slide handing head on a bearing surface of the closure body.

In an embodiment, the bearing surface of the closure body includes a cam, for example a cam roller. It would be appreciated by those persons skilled in the art, however, that the bearing surface could have a low resistance surface, such as a metallic or plastic surface, and the slide handling head contact surface is arranged to slideably contact against the bearing surface of the closure body. In any case, the cam roller or the bearing surface is arranged to slideably or rollably move in relation to the contact surface of the slide handling head. In one embodiment, the cam may be a fixed bush comprising low friction material such as nylon, Teflon or other such low friction material.

In an embodiment, the slide treatment module includes a latch for retaining the closure body in the closed position that is opened by a corresponding surface on the slide handling head when the slide transport robot is configured by the controller to move a slide to the slide treatment module. With reference to the above described embodiment of the detent, it will be appreciated by those persons skilled in the art that the detent works in much the same way as a latch. The detent is arranged to cooperate with a recess in the closure body in the closed position to detain the closure body in the closed position against any opening biasing force. In this embodiment, the bearing surface is disposed at one end of the detention arm so that the slide handling head contacts against the bearing surface of the closure body of a slide treatment module to release the closure body from the detent so as to pivot the closure body to the open position about a pivot disposed on the slide treatment module.

In an embodiment, the slide treatment module includes an opening biasing means for applying biasing force to the closure body to pivot the closure body to the open position. In another embodiment, the slide treatment module further includes a closing biasing means for applying biasing force to the closure body to pivot the closure body to the closed position. For example, the biasing means are springs and the opening biasing means biases the slide treatment module to the open position with a force of approximately 5 N and the closing biasing means is a larger spring that applies a closing force of approximately 45 N.

In an embodiment, the closure body stays in the open position, with say a further detent, until the slide handling head moves the closure body of the slide treatment module back to the closed position by say disengaging the further detent.

In an embodiment, the cam roller protrudes from the closure body and is contacted by a protruding contact member of the slide handling head. That is, the slide handling head contact surface is a protruding contact member surface that contacts the cam roller which rollably moves relative to the protruding contact member when the slide transport robot moves in the x direction to open and close the closure body of the slide treatment module. Furthermore, the cam roller is disposed at one end of an arm protruding from the closure body to define a gap therebetween corresponding in shape to the protruding contact member of the slide handling head. Thus, with reference to the above embodiment, the protruding contact member of the slide handling head can slideably move into the gap between the cam roller and the arm protruding from the closure body when the slide handling head of the slide transport robot moves in the x direction to open the closure body.

In an embodiment, the slide transport device protrudes from the slide handling head adjacent the protruding contact member and is spaced apart from the contact member so as to provide a gap therebetween. Accordingly, in use, when the closure body is pivoted from the closed to the open position, one end of the closure body extends into the gap between the spaced apart protruding contact member and the slide transport device, and part of the protruding contact member extends into the gap provided between the arm and the cam roller. The size of the slide transport robot can thus be minimised to minimise the size of the slide treatment apparatus, allow more slide treatment modules, and/or enable faster locating of slides in the treatment modules.

In an embodiment, the slide transport device includes a gripping device to releasably hold the slides. The gripping device may be mounted for independent horizontal and vertical movement during slide transfer from a slide tray or the like to a predetermined area, such as a slide treatment module. For example, the gripping device includes any device that can grip a slide. For example, the gripping device includes a finger or plurality of fingers that extend from a base to grip an object that is one of a plurality of object types. In an embodiment, the finger includes, or is, a suction device to releasably hold the slides. For example, the suction device includes a suction cup or a bellowed suction cup. It will be appreciated by those persons skilled in the art, however, that the slide transport device also includes other devices to releasably hold the slides, such as a gripper, that may have a hook arranged to grasp and lift a predisposed hooking point on a slide for, say, slides dedicated to a particular slide treatment apparatus. It will also be appreciated that the slide transport device is adjustable to cater for differently dimensioned slides or variations in the surface of a slide, such as a variation resulting from an incorrectly or damaged slide label.

Also, the finger includes a releasing device in addition to the suction device that assists in releasing suction of the slides. That is, for example, a finger adjacent a suction cap can apply a force to the slide that is held by suction to release the suction so that the slide can be released in, say, the slide treatment module.

In another embodiment, the slide handling head includes an indicia reader configured to read a label (e.g. a writeable RFID tag or an image such as a barcode) disposed on the slides. In the embodiment, the indicia reader is configured to read the label (and, in some cases, write thereto with respect to, say, the writeable RFID tag) to receive information indicative of instructions for the controller to treat the one or more tissue samples disposed on the corresponding slides. For example, the instructions include a predetermined order and amount of reagents to be dispensed to the slide by the fluid dispensing robot so as to treat the one or more tissue samples on the slide in the slide treatment module accordingly. In addition, the instructions may also include temperature information, incubation times for the slide, patient information, the priority of the slide in a workflow of the laboratory, etc.

In an embodiment, the slide transport robot is further configured by the controller to move the slides to and from a coverslipping module for coverslipping the slides. For example, the coverslipping module lifts and separates a single coverslip from a stack of coverslips and applies the coverslip, and a mountant in some cases, to the slide. A coverslip may be applied to the slide after contact of the slide with a planar support or without substantial contact with a planar support. In an embodiment, the slide transport robot supports the slide without a planar support during the application of the coverslip.

It will also be appreciated by those persons skilled in the art that the slide transport robot is configured by the controller to move the slides to and from other modules in the slide treatment apparatus, such as an input and an output buffer for adding and removing the slides from the apparatus, and a wash module for washing a dispensing probe of the at least one fluid dispensing robot. Other modules include a mixing module to mix and aspirate reagents therein. For example, the FTP robot is configured to dispense reagents into a mixing module container to mix these reagents on board the apparatus 12 and to subsequently dispense the mixed reagents to a slide.

In an embodiment, the slide transport robot is combined with the at least one fluid dispensing robot. For example, the slide transport robot is combined with a fluid transport robot of the slide treatment apparatus which is configured by the controller to dispense a plurality of high value reagents to slides in the slide treatment modules. In the example, the slide handling head, the slide transport device, and a probe for the fluid transport robot are co-located at one end of the combined slide transport and fluid transport robot so as to further minimise the size of the slide treatment apparatus. Furthermore, in the embodiment, the location of the probe, the slide handling head and the slide transport device correspond to the shape of the slide treatment modules to minimise the size of the slide treatment apparatus. A fluid transport robot is described in the co-pending U.S. provisional patent application entitled "A Fluid Transport System" 61/721,269 having a filing date of 1 Nov. 2012, the contents of which are hereby incorporated herein by reference.

According to another aspect of the present invention there is provided a method of transporting slides for treatment of one or more tissue samples disposed on the slides whereby ones of the slides are received in a plurality of slide treatment modules and a plurality of reagents are dispensed by at least one fluid dispensing robot to said ones of the slides received in the slide treatment modules to treat said one or more tissue samples respectively, the method including: releasably holding the slides with a slide transport device disposed on a slide transport robot; moving the slides to and from the slide treatment modules with the slide transport robot; moving a slide handling head of the slide transport robot to move a closure body of one of the slide treatment modules normally held in a closed position to an open position when the slide transport robot moves one of the slides to the slide treatment module; and releasing said one of the slides so as to locate the slide in the slide treatment module when the closure body is in the open position.

As described, in one embodiment, the closure body of the slide treatment module is biased to the closed position and reverts to the closed position after the slide transport robot locates a slide in a slide treatment module or after it removes a slide from the module. In another embodiment, the closure body of the slide treatment module stays in the open position after the slide transport robot locates a slide therein until it is closed by further action of the slide handling head. In this embodiment, the method further includes moving the slide handling head of the slide transport robot to resist movement of the closure body, normally biased in a closed position, to control movement of the closure body to the closed position.

According to another aspect of the present invention there is provided a computer program code which when executed by a controller implements the above method.

According to another aspect of the present invention there is provided a tangible computer medium comprising the above computer program code.

According to yet another aspect of the present invention there is provided a data file comprising the above program code.

BRIEF DESCRIPTION OF THE DRAWINGS

Embodiments of the present invention will now be described, by way of example only, with reference to the accompanying drawings, in which:

FIG. 12 is a perspective view of a slide treatment module according to an embodiment of the present invention; and FIG. 13 is an end view of a slide treatment module according to an embodiment of the present invention.

DETAILED DESCRIPTION

Figure 1:
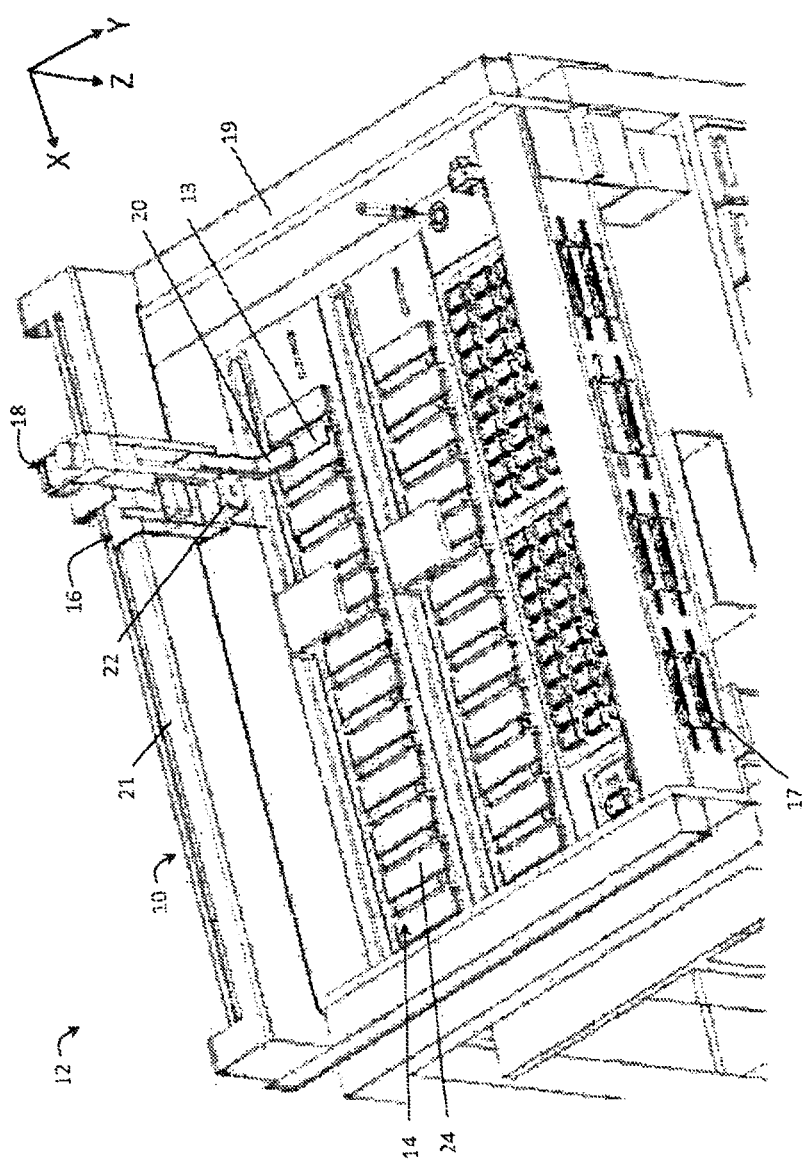
FIG. 1 is a perspective view of an automated slide treatment apparatus having a slide transport system according to an embodiment of the present invention.

A slide transport system 10 for an automated slide treatment apparatus 12 for treating tissue samples disposed on slides 13 is shown in FIG. 1. It can be seen that the slide treatment apparatus 12 includes a plurality of slide treatment modules 14 arranged to receive the slides 13, and includes at least one fluid dispensing robot 16 configured by a controller (not shown) to dispense a plurality of reagents to the slides in the slide treatment modules 14 to treat tissue samples on the slides and a slide transport robot 18 configured by the controller to move the slides 13 to and from the slide treatment modules 14. It will be appreciated by those persons skilled in the art that the controller of the automated slide treatment apparatus 12—and the slide transport robot 18 and the at least one fluid dispensing robot 16—can either be implemented remotely from the apparatus 12 (e.g. implemented by a computer remote from the apparatus) or can be implemented locally with respect to the apparatus 12. In addition, more than one controller can be employed by the apparatus 12; for example, a controller for the fluid dispensing robot 16 and the slide transport robot 18. In any case, it will also be appreciated that the controller includes a number of modules, implemented by a processor and a memory for storing instructions for the modules, to provide instructions to the slide transport robot 18 and the at least one fluid dispensing robot 16 to control movement thereof and dispensing of reagents.

In one embodiment, the slide transport robot 18 is a gantry robot configured by the controller to move the slides 13 to and from the slide treatment modules 14. In the embodiment, the slide transport robot 18 is combined with a fluid dispensing robot 16 in the gantry robot, which is configured to move in the x, y and z axes. It will be appreciated by those persons skilled in the art that the slide transport robot 18 can be independent from the fluid dispensing robot 16. For example, the slide transport robot 18 can be an articulated armed robot while the fluid dispensing robot 16 can be a gantry robot, and vice versa. In the embodiment shown in the Figures, however, the fluid dispensing robot 16 is a fluid transfer probe (FTP) robot configured by the controller to dispense a plurality of high value reagents stored in reagent containers (not shown) to the slides 13 in the slide treatment modules 14. Examples of high value reagents include chromogens and antibodies. That is, as shown in this embodiment, the gantry robot includes the combined FTP robot 16 and the slide transport robot 18 to minimise the size of the apparatus. In any event, as can be seen in the Figures in relation to the apparatus 12, the x axis is a length of the apparatus 12, the y axis is a width of the apparatus 12 and the z axis corresponds to a height of the apparatus 12.

As will be appreciated, the slide transport robot 18 is configured by the controller to move quickly between the different modules in the apparatus 12 in the three axes so as to efficiently move slides in and out of the slide treatment modules 14 so as to treat samples disposed on the slides in the slide treatment modules 14. For example, the slide transport robot 18 is configured to move from one corner of the apparatus 12 to the diagonally opposite corner in 2.2 seconds (which represents the maximum move with respect to the apparatus 12). The travel profiles for the example of the slide transport robot 18 shown with respect to the apparatus 12 in FIG. 1 are: 780 mm in the x axis, 500 mm in the y axis and 120 mm in the z axis although these ranges are examples only. It can also be seen that the gantry robot 18 and the FTP robot 16 moves along a rail 21 in the x direction and a rail 19 in the y direction so as to move slides to and from the slide treatment modules 14 so as to dispense a plurality of reagents to the slides received in the slide treatment modules 14.

Figure 2:
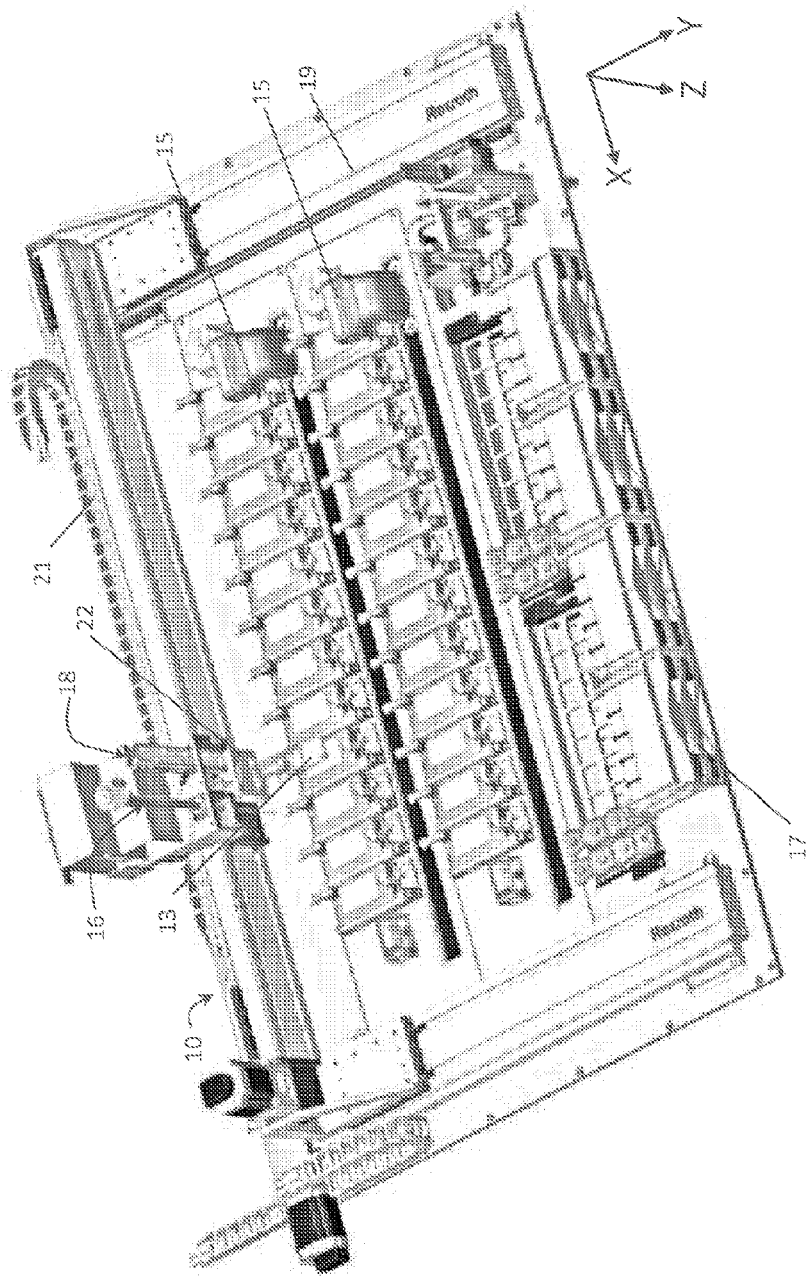
FIG. 2 is a further perspective view of an automated slide treatment apparatus having a slide transport system according to an embodiment of the present invention.

As shown in the embodiment of FIG. 2, the apparatus 12 includes two bulk fluid robots (BFRs) 15 to dispense high volume reagents and the FTP robot 16 to dispense low volume reagents. That is, the BFRs 15 are configured by the controller to dispense a plurality of lesser value reagents (e.g. bulk or high volume reagents) stored in reagent containers to the slides 13 received in the slide treatment modules 14 to also treat tissue samples on the slides 13. That is, in some cases, to treat the tissue samples on the slides 13, a designated combination and order of high and lesser value, bulk reagents is dispensed to the slide. It will be appreciated by those persons skilled in the art that the apparatus 12 may include more than two BFRs to dispense the lesser value reagents stored in reagent containers to the slides 13.

For example, the BFRs 15 are configured by the controller to dispense bulk reagents to the slides 13, such as solutions of oxalic acid, sulphuric acid, potassium permanganate, alcohol, dewaxing agent, dyes such as haematoxylin, peroxide, distilled water and buffer to treat the tissue samples disposed thereon. It can also be seen in FIG. 2 that there is a BFR 15 for each row of slide treatment modules 14 and that the slide transport robot 18 is configured to move the slides 13 to and from the slide treatment modules 14 without interfering with the BFRs 15 as the slide transport robot 18 can move in the z direction. Indeed, the BFRs 15 are configured to move only in two directions, (the x and z directions shown) to dispense the bulk reagents to the slides 13 in the slide treatment modules 14.

Figure 5:
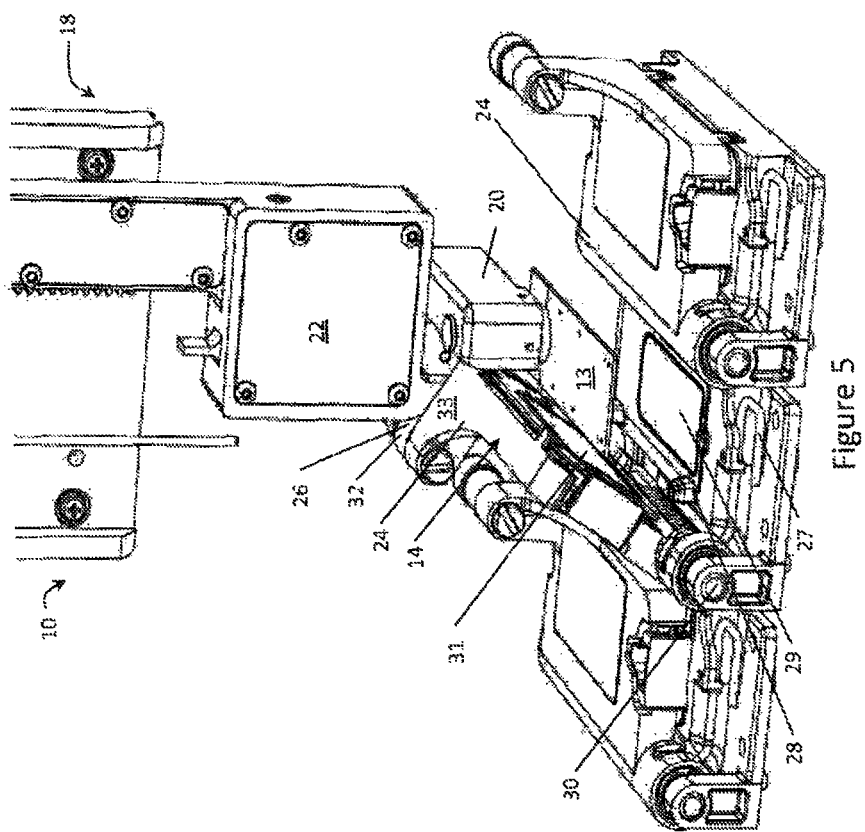
FIG. 5 is a perspective view of the slide transport system of FIG. 3 in use having opened a closure body of a slide treatment module to locate a slide therein.

The slide transport system 10 also includes a slide transport device 20, shown in say FIG. 5, disposed on the slide transport robot 18, which is configured by the controller to releasably hold the slides 13. For example, the slide transport device 20 includes a suction cup arranged to releasably hold the slide 13 when it is to be moved to a slide treatment module 14 and to release the slide 13 to locate it in the slide treatment module 14. As described, the slide transport device 20 is envisaged to include other means for releasably holding a slide, such as a gripper.

Furthermore, the slide transport robot 18 includes a slide handling head 22 arranged to move a closure body 24, shown in more detail in FIG. 5, of one of the slide treatment modules 14 so as to move the closure body 24 normally biased in a closed position to an open position when the slide transport robot is configured by the controller to move one of the slides 13 to the slide treatment module 14. The slide transport device 20 is then configured by the controller to release the slide 13 so as to locate the slide 13 in the slide treatment module 14 when the closure body 24 is in the open position (as shown more clearly in FIG. 5).

FIGS. 1 and 2 also show the automated slide treatment apparatus 12 having input and output buffers in the form of an access module 17, whereby the input buffer of the access module 17 introduces slides 13 to the apparatus 12 for treatment and the output buffer of the access module 17 allows for the removal of the slides 13 from the apparatus 12 after treatment of the tissue samples on the slides 13. The slide transport robot 18 of the embodiment is thus further configured to retrieve a slide from the access module 17 and locate it in a slide treatment module 14 and to remove the slide 13 from the slide treatment module 14 and locate it in the access module 17 after the tissue samples disposed on the slide have been treated. In addition, the slide transport robot 18 of the embodiment can also be configured to move the slide to/from other modules (not shown) for performing other operations on the slide, such as coverslipping and digital imaging modules, before moving the slide 13 to the access module 17.

Also not shown is a calibration module which calibrates the position of the slide treatment robot 18 within the automated slide treatment apparatus 12. Here, the calibration module is disposed at a known location in the automated slide treatment apparatus 12 with known x, y and z coordinates so that the slide treatment robot 18 can calibrate its perceived location with the actual location at designated time intervals.

Figure 3:
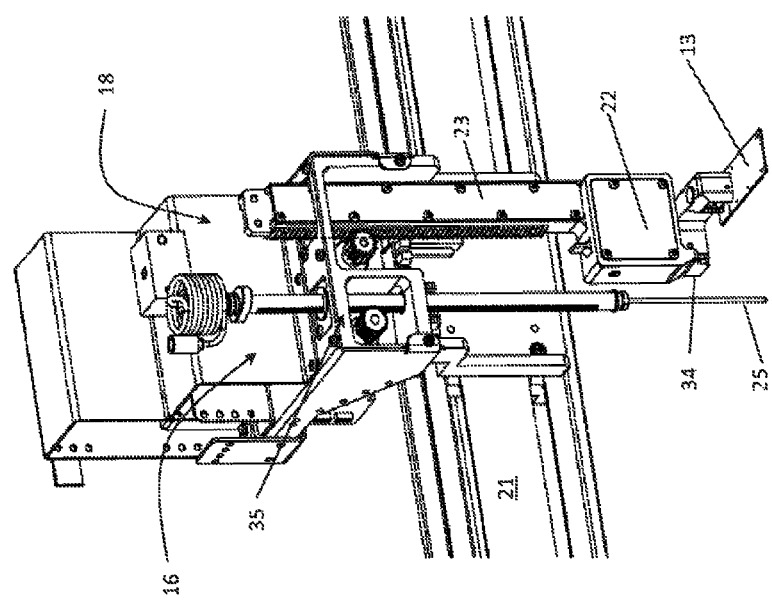
FIG. 3 is a perspective view of a slide transport system for an automated slide treatment apparatus according to an embodiment of the present invention.
Figure 4:
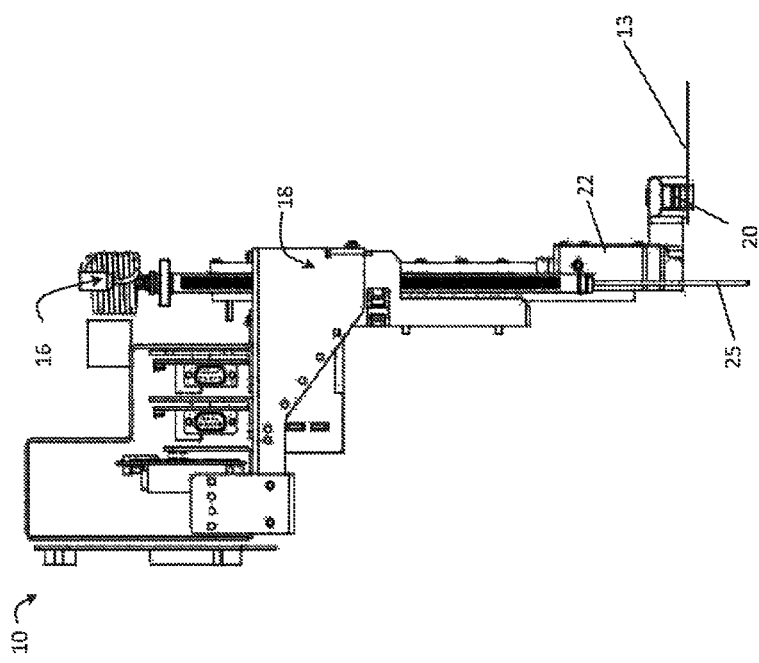
FIG. 4 is a side view of the slide transport system of FIG. 3.

FIGS. 3 and 4 show the slide transport robot 18 in further detail. The slide transport robot 18 is configured to move along the rail 21 in the x axis and along a rack 23, of a rack and pinion drive system, in the z axis so as to locate a slide 13 in the slide treatment module 14 when the closure body 24, shown in FIG. 5, is held in the open position by the slide handling head 22. The rack 23 is driven by a pinion on the robot 18 to lower and raise the slide 13 in the z axis. In this embodiment, the slide transport robot 18 moves along the rail 21 and the rail 19 in the x and y axes, as shown in FIG. 2, using a chain drive system driven by stepper motors.

Nonetheless, it will be appreciated by those persons skilled in the art that other drive systems may be employed, such as another further rack and pinion or belt drive system, pneumatic, solenoid, or lead screw systems.

The FTP robot 16 is also shown in more detail, in FIGS. 3 and 4, which is combined with the slide transport robot 18. The FTP robot 16 is configured to move in the x axis using the above described chain drive system and to dispense the reagents to the slide 13 in the slide treatment module 14 (not shown) with a probe 25. The probe 25 can be raised or lowered in the z axis by another rack and pinion drive system 35 so that the reagents can be dispensed to the slide 13 when the closure body 24 of the slide treatment module 14 is in the closed position. It will be appreciated by those persons skilled in the art that, in one embodiment, the probe 25 and the slide transport device 20 can be raised or lowered in the z axis by the same drive mechanism. In any event, the FTP robot 16 is described in more detail in the co-pending U.S. provisional patent application 61/721,269 entitled "A Fluid Transport System", having a filing date of 1 Nov. 2012.

FIGS. 5 and 6A-C show a snapshot of the slide treatment apparatus 12 in use. In particular, they show the slide transport robot 18 of the slide transport system 10 engaging with the slide treatment module 14 to locate a slide 13 in the slide treatment module 14 for dispensing of reagents and thus treatment of tissue samples on the slide 13. Here it can be seen that the slide handling head 22 of the slide transport robot 18 is arranged to contact against a bearing surface 26 of the closure body 24 to move the closure body 24 to the open position. More particularly, it can be seen that the slide handling head 22 contacts against the bearing surface 26 when the slide transport robot 18 moves in the x axis to move the closure body 24 to the open position. As described, the slide treatment modules 14 are aligned in the apparatus 12 so as to be opened in the x direction to minimise the amount of movement for the slide transport robot 18.

The slide handling head 22 of the slide transport robot 18 contacts against the bearing surface 26 of the closure body 24 to pivot the closure body 24 about a pivot 30 to the open position. The closure body 24 is biased to the closed position with a spring 27 so that the slide handling head 22 contacts against the bearing surface 26 of the closure body 24 of the slide treatment module 14 whilst the bias of the closure body 24 urges it to the closed position both when the slide transport robot 18 moves in the x direction to locate the slide 13 in the slide treatment module 14 and when the slide transport robot 18 removes the slide from the slide treatment module 14.

The slide transport robot 18 further moves in the x and y axes when the closure body 24 is in the open position to further (e.g. better) locate the slide 13 in the slide treatment module 14 using at least one reference datum point 28 disposed on the slide treatment module 14. That is, the slide transport robot 18 stops moving the slide 13 in the slide treatment module in the x and/or y axes when the slide touches the reference data points 28. In addition, the slide treatment module 14 includes a mounting surface 29 (e.g. floor) of the slide treatment module 14 and the slide transport robot 18 stops moving the slide 13 in the slide treatment module in the z axes when the slide 13 touches the mounting surface 29.

The spring 27 can also bias the closure body 24 to the closed position to achieve a seal with the slide 13 and the mounting surface 29 to create a sealed reaction chamber— for example, substantially the size of the slide—for treating the tissue samples on the slide 13 with the use of a cover member 31 of the slide treatment module 14. The cover member 31 is disposed on the underside of the closure body 24 and is arranged to form the sealed reaction chamber with the slide 13 when the closure body 24 is in the closed position after the slide transport robot 18 has located the slide 13 in the slide treatment module 14. Details of the cover member is described in the co-pending U.S. provisional patent application 61/721,280 entitled "Slide Staining Assembly and Cover Member", having a filing date of 1 Nov. 2012. The FTP robot 16 and the BFR 15 can then dispense reagents to the slide 13 in the slide treatment module 14 when the closure body 24 is in the closed position in the designated order and with designated volumes. It will be appreciated by those persons skilled in the art that the instructions and the order can be stored in a memory in data communication with the controller.

Figure 7:
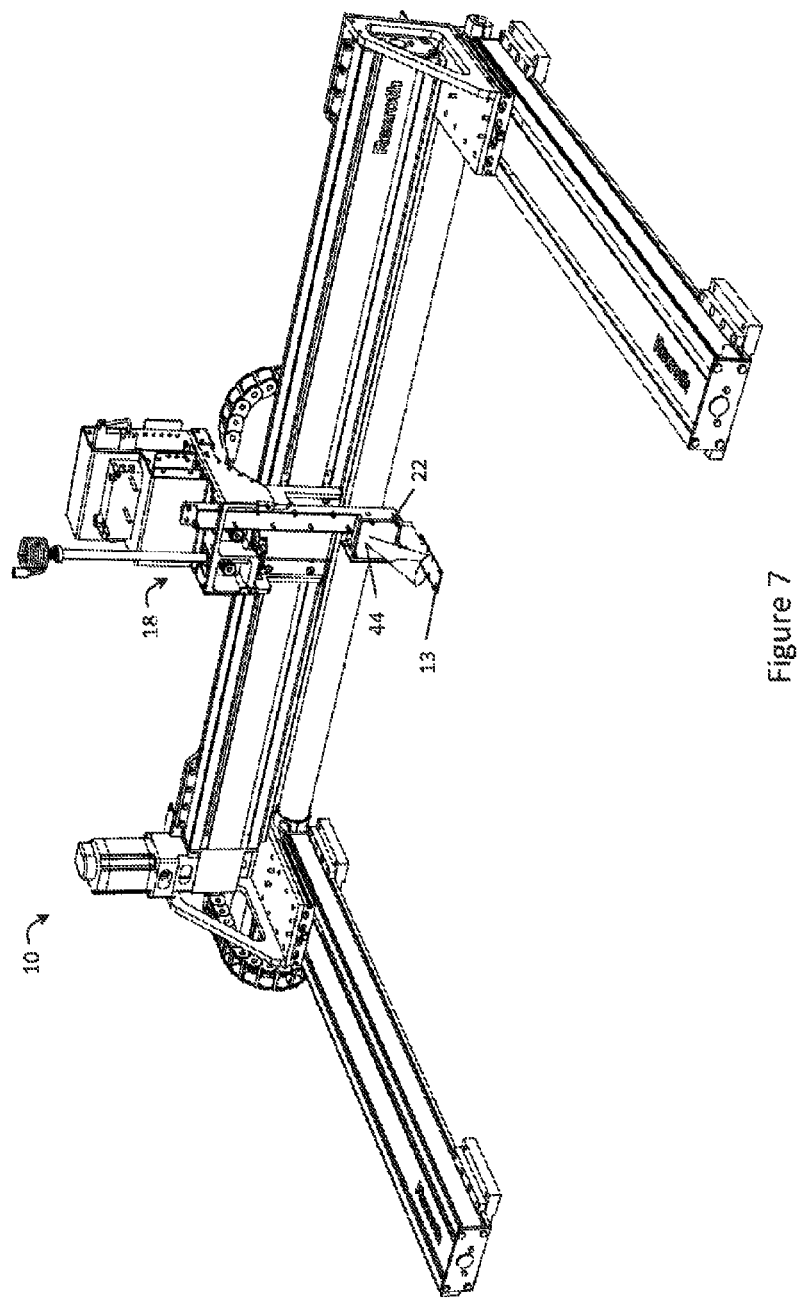
FIG. 7 is a perspective view of a slide transport system according to an embodiment of the present invention.
Figure 8:
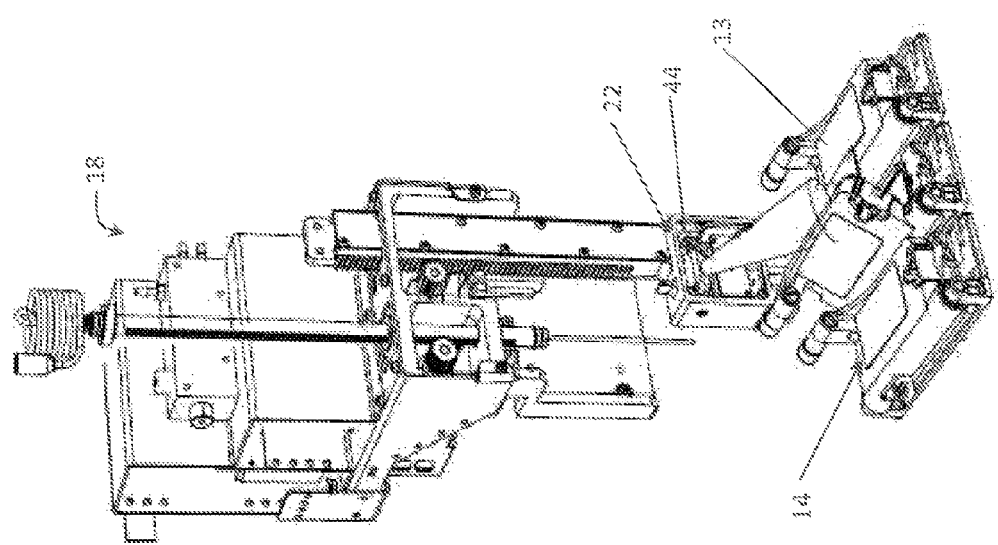
FIG. 8 is a further perspective view of the slide transport system having moved a closure body of a slide treatment module to locate a slide therein.

In another embodiment, the instructions, or at least part thereon, are stored on each of the slides 13 in the form of a label that is read by an indicia reader 44, as shown in FIGS. 7 and 8 (showing a light path extending from the indicia reader 44). In this embodiment, the slide handling head 22 includes the indicia reader 44 which is disposed at an angle to the slide handling head 22 and is configured to read labels disposed on the slides 13 to receive information indicative of instructions for the controller to treat the tissue samples disposed on the corresponding slides. It will be appreciated by those persons skilled in the art that, in some cases, the label will include complete instructions to treat samples disposed on the slides and, in some other cases, it will contain part instructions or a link to stored instructions for the controller to implement the method of treatment.

For example, the indicia reading device 44 acquires data, such as Label ID, liquid level sensor information, reagent IDs and calibration data, from a label in for form of, say, a 1D, 2D or 3D barcode, or an RFID, OCR or integrated circuit disposed on the slide 13. Other data includes protocol information, sample/case ID, and pathologist/other lab information.

As described, the closure body 24 and the slide transport robot 18 are arranged so that movement of the slide transport robot 18 opens and closes the closure body 24 of the slide treatment module 14. Specifically, in the embodiment shown in, for example, FIG. 5, the bearing surface 26 of the closure body 24 includes a cam roller 32 protruding from the closure body 24 at a distal end of an arm 33 protruding from the closure body 24. Also, the slide handling head 22 of the slide transport robot 18 includes a protruding contact member 34 arranged to contact the cam roller 32 to move the closure body 24 to the open position. Thus, in use, the slide handling head 22 of the slide transport robot 18 contacts against the bearing surface 26 of the closure body 24 of a slide treatment module 14 to pivot the closure body 24 about the pivot 30 to the open position and back to the closed position after locating or removing a slide therein.

Figure 6:
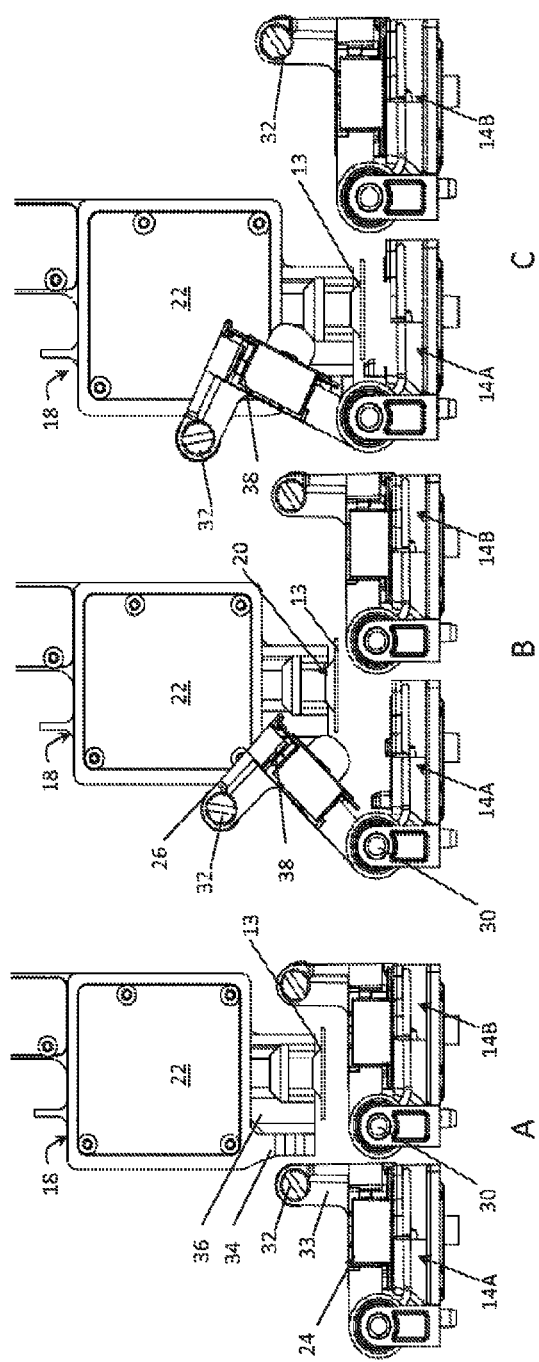
FIG. 6A is a front view of the slide transport system of FIG. 3 located adjacent a closure body of a slide treatment module.
FIG. 6B is a further front view of the slide transport system of FIG. 6A having opened the closure body of the slide treatment module.
FIG. 6C is a further front view of the slide transport system of FIG. 6A and 6B locating a slide in the slide treatment module.

It can be seen from FIGS. 6A to 6C that the cam roller 32, disposed on the end of the arm 33, protrudes from the closure body 24 to define a gap bordered on two sides corresponding (at least partially) in shape to the protruding contact member 34 of the slide handling head 22. The slide transport device 20, including the suction cup and associated suction mechanism, also protrudes from the slide handling head 22 adjacent the protruding contact member 34 and is spaced apart from the protruding contact member 34 so as to provide a gap 36 there between, shown most clearly in in FIG. 6A. Thus, in use, when the closure body 24 is pivoted from the closed to the open position, as shown in FIGS. 6A, B and C, one end 38 of the closure body extends into the gap 36 between the spaced apart protruding contact member 34 and the slide transport device 20, and part of the protruding contact member 34 extends into the gap provided between the arm 33 and the cam roller 32.

That is, firstly, in FIG. 6A, the slide transport robot 18 is located adjacent a first slide treatment module 14A for a slide 13 to be located therein, and then, in FIG. 6B, the robot 18 moves the slide 13 in the x axis to locate it in the slide treatment module 14A by pivoting the closure body 24 about the pivot 30 to an open position. In FIG. 6C, the slide transport robot 18 then moves in the z axis to lower the slide 13 in the slide treatment module 14A so that the slide transport device 20 (e.g. suction cup) can release the slide 13 so as to locate it in the slide treatment module 14A for subsequent treatment.

It can also be seen in FIG. 6A that the protruding slide transport device 20 and the protruding contact member 34 of the slide handling head 22 correspond in size to a slide treatment module 14B. That is, the protruding portions of the slide handling head 22 fit between adjacent cam rollers 32 and protruding arms of the slide treatment modules 14A and 14B so as to maximise the number of slide treatment modules 14 that can be implemented by the apparatus 12. In this way, the slide handling head 22 of the slide transport robot 18 can be located above the slide treatment module 14B adjacent to the slide treatment module 14A before moving the slide treatment module 14A to the open position to locate a slide therein.

Figure 10:
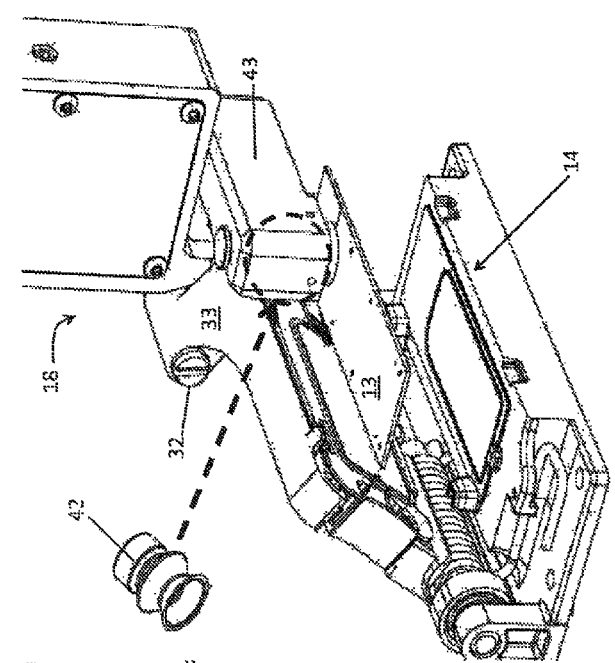
FIG. 10 is a further perspective view of a slide transport system showing a further slide transport device according to an embodiment of the present invention.
Figure 9:
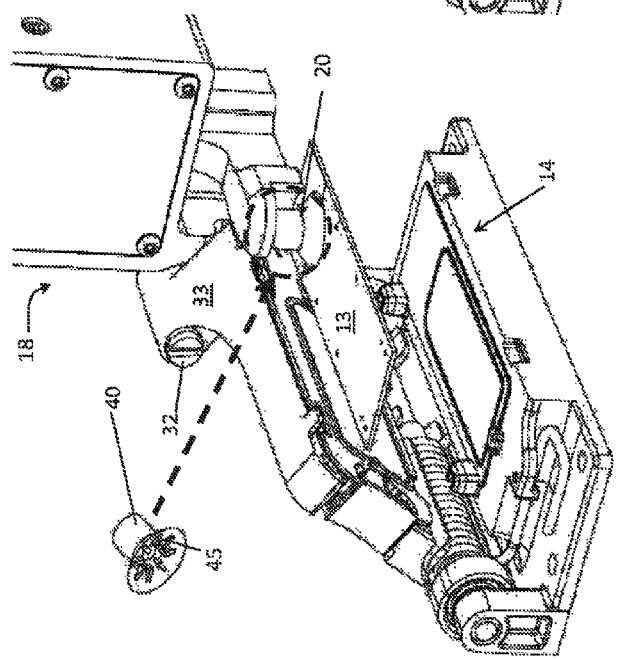
FIG. 9 is a perspective view of a slide transport system showing a slide transport device according to an embodiment of the present invention.

As described, the slide transport device 20 includes a suction cup 40, as shown in FIG. 9. In the embodiment shown in FIG. 10, the slide transport device 20 is a bellowed suction cup 42, which allows for the further application of friction, contained in a housing 43. The suction cups 40 or 42 may be made from a material such as polymeric, elastomeric or plastic material such as nitrile, polyurethane or viton and it can be seen that the suction cup 40 may include internal cleats 45 to ensure the slide is held in place.

It will be appreciated by those persons skilled in the art that the bellowed suction cup 42 includes a vacuum means (not shown in the Figures) for activating the cup that is configured by the controller to releasably hold the slides 13. The suction cup 40 can also be implemented with respect to the vacuum means or it may simply use its cavity and applied pressure to displace air to releasably hold a slide.

Also, the vacuum means may be configured to operate with the use of pressure sensors to maintain pressure and thus grip on the slides. In one embodiment, the vacuum means maintains a positive pressure to avoid the slide sticking to the bellow suction cup 42. In addition, the slide transport device 20 may include additional sensors (not shown), such as an optical sensor or a reflective optoelectronic sensor, for checking whether a slide being held is in the correct position for it to be located accordingly.

FIGS. 12 and 13 show a further embodiment of the slide transport system 10 where the closure body 24 is detained in the closed position with a detent 46 protruding from a detention arm 37 that is arranged to cooperate with a recess 48 in the closure body 24 in the closed position. Accordingly, the closure body 24 can be detained in the closed position against the action of an opening bias or it can be detained to prevent accidental opening of the closure body 24 of the slide treatment module 14. In the embodiment shown, the slide treatment module 24 includes two opposing biasing means. Specifically, an opening biasing means 52 for applying biasing force to the closure body 24 to pivot the closure body 24 to the open position and a larger, closing biasing means 50 for applying biasing force to the closure body 24 to pivot the closure body 24 to the closed position. As shown, the biasing means are springs and, for example, the opening biasing means 52 applies a force of approximately 5 N and the closing biasing means 50 applies a closing force of approximately 45 N.

In this embodiment, the bearing surface 26 is disposed at one end of the detention arm 37 so that the slide handling head 22, specifically the protruding contact member 34 of the slide handling head 22, contacts against the bearing surface 26 to move the closure body 24 to the open position. Also, it can be seen that the bearing surface 26 includes the cam roller 32 described above at one of its ends. Thus, in use, the protruding contact member 34 contacts against the cam roller 32 to release the recess 48 of the closure body 24 from the detent 46 so as to pivot the closure body 24 to the open position about the pivot 30 disposed on the slide treatment module 14. Action of the the slide handling head 22 of the slide transport robot 18, after releasing the detent 46, therefore pivots the closure body 24 about the pivot 30 to the open position and back to the closed position after locating or removing a slide therein as described above.

Figure 14:
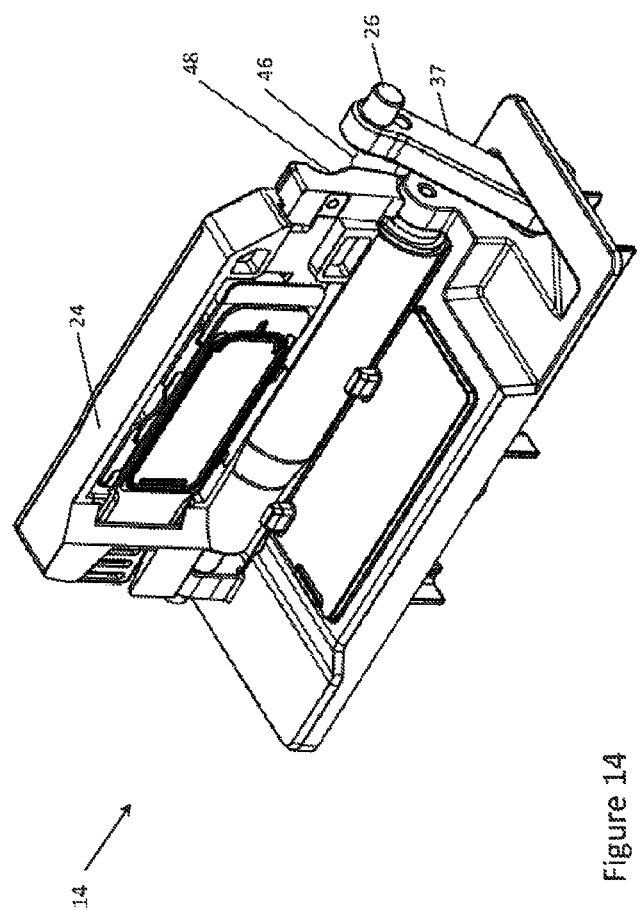
FIG. 14 is a perspective view of an open slide treatment module according to an embodiment of the present invention.

FIGS. 13 and 14 show the detention arm 37 in further detail. The detention arm 37 includes a detention pivot 54 at an opposed end to the cam roller 32 that is retained by a section of the slide treatment module 14. The detention arm 37 rotates about detention pivot 54 as it is moved by the slide handing head 22 between the open and closed positions of the closure body 24. FIG. 13 shows the detention arm 37 in the closed position with the detent 46 within the recess 48 (not shown in the Figure). FIG. 14 shows the detention arm 37 in the open position with the detent 46 disengaged from the recess 48. In use, the action of the slide handling head 22 rotates the detention arm 37 around detention pivot 54 so that the end with the detent 46 tracks along the top of the closure body 24 to its open position and the closure body 24 is consequently moved to the open position to an angle determined by the angle of the endstop 56. It will be appreciated that, in the open position, the detent 46 is moved away from the recess 48 of the closure body 24.

Furthermore, it is envisaged by those persons skilled in the art that movement means other than biasing means can be employed by the slide transport system 10 to open and close the closure body 24 of the slide treatment module 14. For example, after the detent 46 is released, a motor (not shown) may drive the closure body 24 to the open position until reaching its final position that is bound by the movement of the detention arm 37. The motor may also drive the closure body 24 back to the closed position. In one example, the motor is a screw drive motor.

In another example, the detent 46 is an electromagnetic detent that is configured to detain the closure body 24 in the closed position when say a current is applied. In this example, the electromagnetic detent can be released by the slide handling head 22 moving against the cam roller 32 to open the current circuit.

Figure 11:
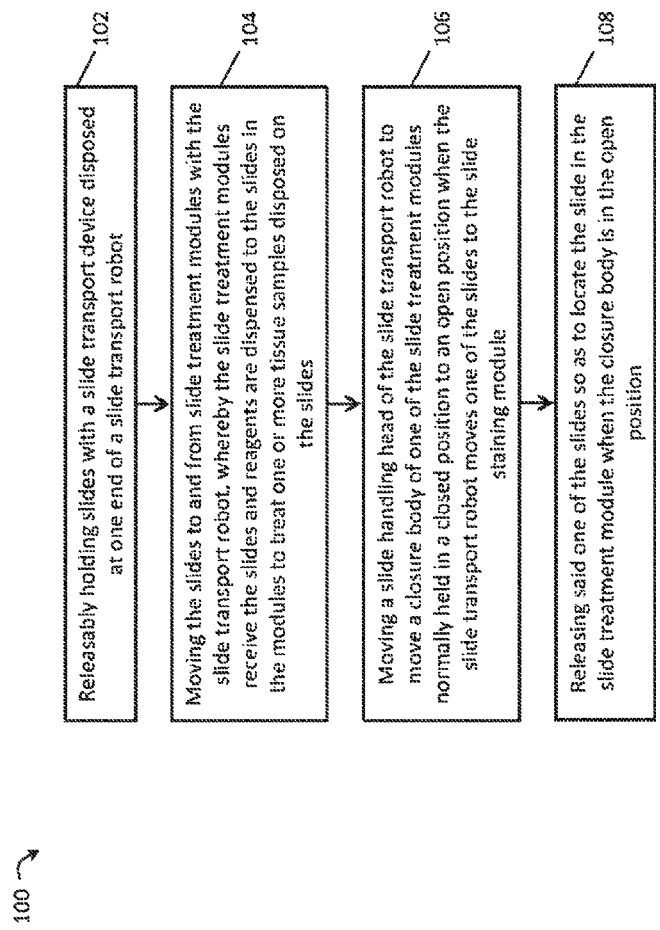
FIG. 11 is a flow chart of a method of transporting slides for treatment of tissue samples disposed on the slides according to an embodiment of the present invention.

Referring back to FIG. 11, there is shown a summary of a method of transporting 100 slides for treatment of one or more tissue samples disposed on the slides. The method includes the steps of releasably holding 102 slides with a slide transport device disposed at one end of a slide transport robot, moving 104 the slides to and from slide treatment modules with the slide transport robot, whereby the slide treatment modules receive the slides and reagents are dispensed to the slides in the modules to treat one or more tissue samples disposed on the slides, moving 106 a slide handling head of the slide transport robot to move a closure body of one of the slide treatment modules normally held in a closed position to an open position when the slide transport robot moves one of the slides to the slide treatment module, and releasing 108 said one of the slides so as to locate the slide in the slide treatment module when the closure body is in the open position.

Further aspects of the method will be apparent from the above description of the slide transport system 10. A person skilled in the art will also appreciate that a method could be embodied in a program code. The program code could be supplied in a number of ways, for example on a tangible computer readable medium, such as a disc or a memory.

It is to be understood that various alterations, additions and/or modifications may be made to the parts previously described without departing from the ambit of the present invention, and that, in the light of the above teachings, the present invention may be implemented in software, firmware and/or hardware in a variety of manners as would be understood by the skilled person.

The discussion of documents, acts, materials, devices, articles and the like is included in this specification solely for the purpose of providing a text for the present invention. It is not suggested or represented that any of these matters formed part of the prior art base or were common general knowledge in the field relevant to the present invention as it existed before the priority date of each claim of this application.

Where the terms "comprise", "comprises", "comprised" or "comprising" are used in this specification (including the claims) they are to be interpreted as specifying the presence of one or more features, but not precluding the presence or addition of further features in various embodiments of the invention.

The invention claimed is:

1. A slide transport system for an automated slide treatment apparatus for treating one or more tissue samples disposed on slides including a plurality of slide treatment modules arranged to receive ones of the slides and at least one fluid dispensing robot configured by a controller to dispense a plurality of reagents to said ones of the slides received in the slide treatment modules to treat said one or more tissue samples respectively, the slide transport system comprising:
   a slide transport robot configured by the controller to move the slides to and from the slide treatment modules, each slide treatment module comprising a closure body which covers a face of the associated slide thereby extending substantially parallel to the face of the slide; and
   a slide transport device disposed on the slide transport robot and configured by the controller to releasably hold the slides,
   the slide transport robot including a slide handling head arranged to move the closure body of one of the slide treatment modules so as to move the closure body from a closed position to an open position as the slide transport robot approaches the closure body,
   wherein the slide transport device is configured by the controller to release the slide so as to locate the slide in the slide treatment module when the closure body is in the open position and,
   wherein the slide handling head is further arranged to contact against a bearing surface of the closure body to move the closure body to the open position.

2. The slide transport system as claimed in claim 1, wherein the slide handling head contacts against the bearing surface of the closure body of said one of the slide treatment modules whilst a bias, provided by a spring, of the closure body moves the closure body to the closed position when the slide transport robot moves in linearly after the slide transport robot locates or removes the slide in the slide treatment module.

3. The slide transport system as claimed in claim 2, wherein the slide handling head contacts against the bearing surface of the closure body of said one of the slide treatment modules to pivot the closure body to the open position about a pivot disposed on the slide treatment module.

4. The slide transport system as claimed in claim 3, wherein, in use, when the closure body is pivoted from the closed to the open position, one end of the closure body extends into the gap between the spaced apart protruding contact member and the slide transport device, and part of the protruding contact member extends into the gap provided between an arm and a cam roller on the closure body.

5. The slide transport system as claimed in claim 1, wherein the closure body is detained in the closed position with a detent protruding from a detention arm that is arranged to cooperate with a recess in the closure body in the closed position.

6. The slide transport system as claimed in claim 5, wherein a bearing surface is disposed at one end of the detention arm.

7. The slide transport system as claimed in claim 6, wherein the slide handling head contacts against the bearing surface of the closure body of said one of the slide treatment modules to release the closure body from the detent so as to pivot the closure body to the open position about a pivot disposed on the slide treatment module.

8. The slide transport system as claimed in claim 7, wherein the slide treatment module further includes an opening biasing means for applying biasing force to the closure body to pivot the closure body to the open position.

9. The slide transport system as claimed in claim 7, wherein the slide treatment module further includes a closing biasing means for applying biasing force to the closure body to pivot the closure body to the closed position.

10. The slide transport system as claimed in claim 1, wherein the slide transport device includes a suction device to releasably hold the slides.

11. The slide transport system as claimed in claim 1, wherein the slide handling head includes an indicia reader configured to read a label disposed on the slides, wherein indicia reader is configured to read the label to receive information indicative of instructions for the controller to treat the one or more tissue samples disposed on the corresponding slides.

12. A method of transporting slides for treatment of one or more tissue samples disposed on the slides whereby ones of the slides are received in a plurality of slide treatment modules and a plurality of reagents are dispensed by at least one fluid dispensing robot to said ones of the slides received in the slide treatment modules to treat said one or more tissue samples respectively, each slide treatment module comprising a closure body which covers a face of the associated slide thereby extending substantially parallel to the face of the slide when in a closed position, the closure body including a bearing surface, the method comprising:
   releasably holding the slides with a slide transport device disposed on a slide transport robot;
   moving the slides to and from the slide treatment modules with the slide transport robot;
   moving a slide handling head of the slide transport robot to move the closure body by contacting against the bearing surface of the closure body to move the closure body to the open position of at least one of the slide treatment modules from the closed position as the slide transport robot approaches the closure body; and releasing said one of the slides so as to locate the slide in the slide treatment module when the closure body is in the open position.

13. A slide treatment apparatus, comprising:
a plurality of slide treatment modules configured to receive slides thereon, said slides having slide surfaces for receiving tissue samples thereon, the slide surfaces being covered by closure bodies respectively which cover respective faces of the slides to thereby extend parallel thereto when in a closed position;
a fluid dispensing robot configured by a controller to dispense a plurality of reagents to the slides received in the slide treatment modules to treat the tissue samples respectively disposed on the slides;
a slide transport robot configured by the controller to move the slides to and from the slide treatment modules, the slide transport robot including:
  a slide transport device configured by the controller to releasably hold the slides;
  a slide handling head arranged to move the closure bodies of the associated slide treatment modules from the closed position to an open position when the slide transport robot is instructed by the controller to move a selected one of the slides to the associated slide treatment module; and
  wherein, the slide handling head is arranged to contact against a bearing surface of the closure body to move the closure body to the open position.

14. The slide treatment apparatus of claim 13, wherein the slide transport robot is combined with said fluid dispensing robot.

15. The slide transport system as claimed in claim 1, wherein the controller is configured to control the slide transport robot such that the slide handling head moves the closure body of one of the slide treatment modules to the open position as the slide transport robot approaches the closure body by interacting the slide handling head with an arm protruding from the closure body.

* * * * *